US012625351B2

(12) United States Patent
Wang et al.

(10) Patent No.: US 12,625,351 B2
(45) Date of Patent: May 12, 2026

(54) IMAGE CAPTURE AT VARYING OPTICAL POWERS

(71) Applicant: Meta Platforms Technologies, LLC, Menlo Park, CA (US)

(72) Inventors: Youmin Wang, Bellevue, WA (US); Yatong An, Redmond, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 295 days.

(21) Appl. No.: 18/367,971

(22) Filed: Sep. 13, 2023

(65) Prior Publication Data

US 2025/0085514 A1    Mar. 13, 2025

(51) Int. Cl.
| | |
|---|---|
| *G02B 13/00* | (2006.01) |
| *A61B 3/113* | (2006.01) |
| *A61B 3/14* | (2006.01) |
| *B81B 3/00* | (2006.01) |
| *G02B 7/09* | (2021.01) |
| *G02B 27/01* | (2006.01) |

(52) U.S. Cl.
CPC .......... *G02B 13/0075* (2013.01); *A61B 3/113* (2013.01); *A61B 3/14* (2013.01); *B81B 3/0021* (2013.01); *B81B 3/0062* (2013.01); *G02B 7/09* (2013.01); *G02B 27/0172* (2013.01)

(58) Field of Classification Search
CPC .. G02B 13/0075; G02B 27/0172; A61B 3/113
See application file for complete search history.

(56) References Cited

U.S. PATENT DOCUMENTS

| | | | |
|---|---|---|---|
| 6,361,167 B1 * | 3/2002 | Su | A61B 3/107 |
| | | | 351/206 |
| 8,711,495 B2 | 4/2014 | Topliss | |
| 10,114,222 B2 * | 10/2018 | Alexander | H04N 9/3161 |
| 2014/0285905 A1 * | 9/2014 | Zhou | G02B 7/10 |
| | | | 359/696 |
| 2019/0199242 A1 | 6/2019 | Wang et al. | |
| 2020/0268296 A1 * | 8/2020 | Alcaide | G06F 3/013 |
| 2021/0231909 A1 * | 7/2021 | Colburn | G02B 7/10 |
| 2022/0206119 A1 | 6/2022 | Lu et al. | |
| 2022/0296094 A1 * | 9/2022 | Ashok | A61B 3/12 |

OTHER PUBLICATIONS

Li L., et al., "MEMS-Based Self-Referencing Cascaded Line-Scan Camera Using Single-Pixel Detectors," Optics Express, Sep. 2, 2019, vol. 27, No. 18, pp. 25457-25469.
Zhou G., et al., "Microelectromechanically-Driven Miniature Adaptive Alvarez lens," Optics Express, Jan. 14, 2013, vol. 21, No. 1, 8 pages.

* cited by examiner

*Primary Examiner* — Cara E Rakowski
(74) *Attorney, Agent, or Firm* — Greenberg Traurig, LLP

(57) ABSTRACT

An imaging device includes an image pixel array and a plurality of micro-electro-mechanical systems (MEMS) Alvarez tunable lenses disposed over regions of the imaging pixels. The MEMS Alvarez tunable lenses are configured to be adjusted to varying optical powers to focus image light to the plurality of imaging pixels at varying focus depths. Processing logic is configured to drive the plurality of MEMS Alvarez tunable lenses to provide varying optical powers to focus the image light to the imaging pixels during a plurality of image captures with the imaging pixels.

20 Claims, 7 Drawing Sheets

230

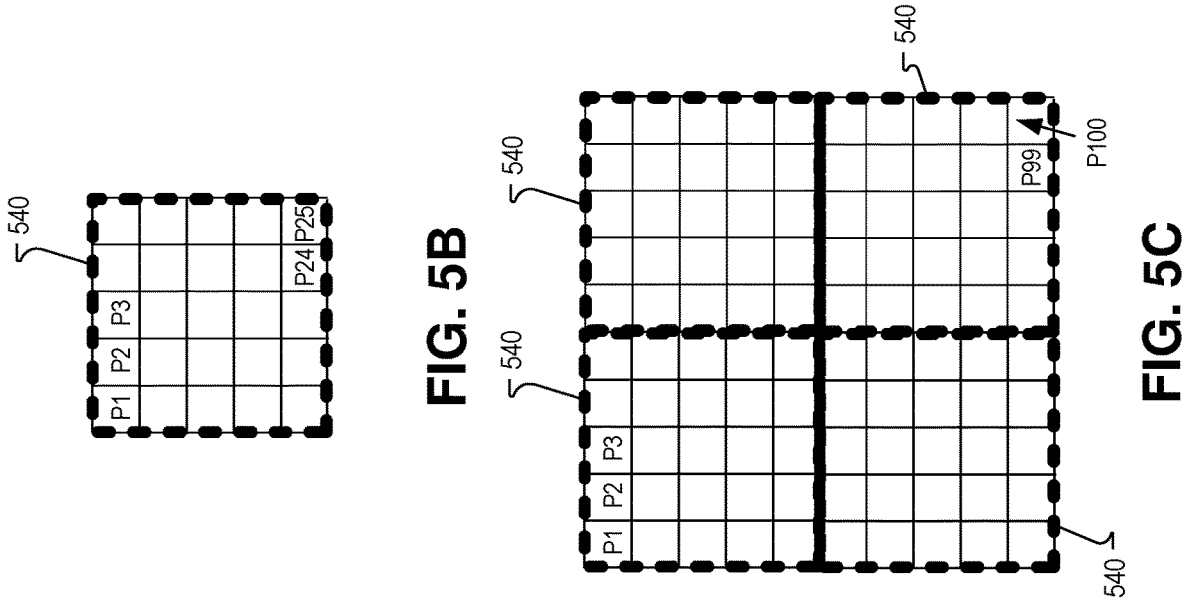
FIG. 5B
FIG. 5C
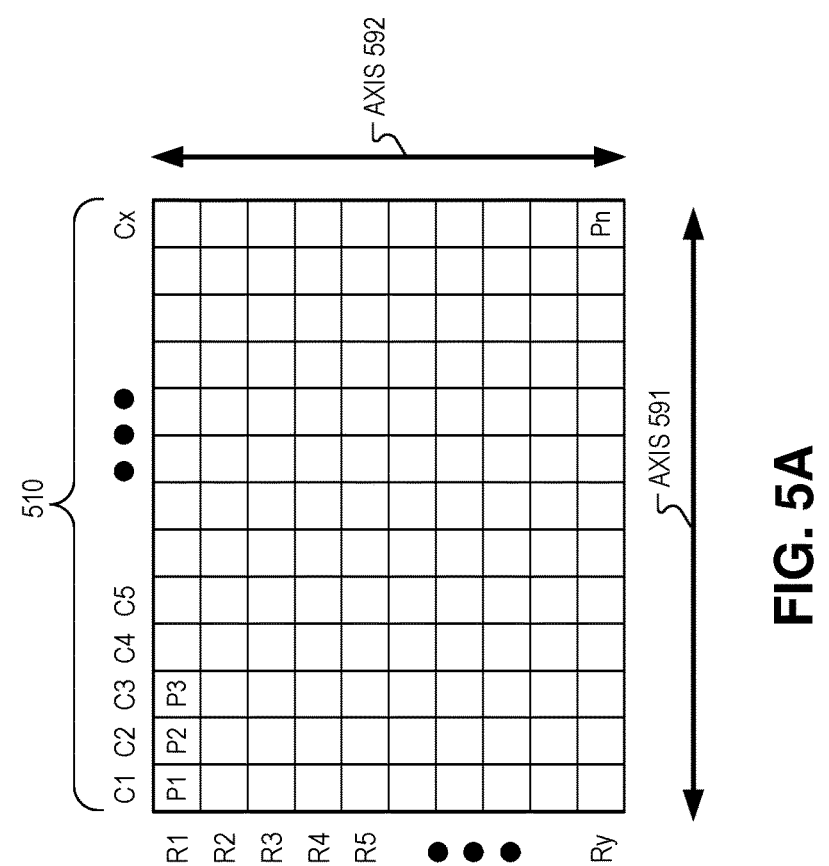
FIG. 5A

IMAGE CAPTURES AT VARYING
OPTICAL POWERS

700

DRIVE MEMS ALVAREZ TUNABLE LENS TO FIRST POSITION — 705

INITIATE FIRST IMAGE CAPTURE WHILE MEMS ALVAREZ TUNABLE LENS IS AT THE FIRST POSITION — 710

DRIVE MEMS ALVAREZ TUNABLE LENS TO SECOND POSITION — 715

INITIATE SECOND IMAGE CAPTURE WHILE THE MEMS ALVAREZ TUNABLE LENS IS AT THE SECOND POSITION — 720

IMAGE CAPTURE AT VARYING OPTICAL POWERS

TECHNICAL FIELD

This disclosure relates generally to optics, and in particular to capturing images at varying optical powers.

BACKGROUND INFORMATION

Light field microscopy includes capturing images at various depths of field. Various "light field cameras" have been sold in the past. Existing systems typically suffer from relatively low speed image capture or require a large number of image pixels to generate images with suitable resolutions.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

FIG. 5A illustrates an example image pixel array having an imaging plane defined in a two-dimensional x-y plane, in accordance with aspects of the disclosure.

FIG. 5B illustrates an example region that a single MEMS Alvarez tunable lens may be disposed over to focus image light to a plurality of the imaging pixels, in accordance with aspects of the disclosure.

FIG. 5C illustrates four MEMS Alvarez tunable lenses configured to focus image light to a plurality of imaging pixels in corresponding regions, in accordance with aspects of the disclosure.

DETAILED DESCRIPTION

Figure 1:
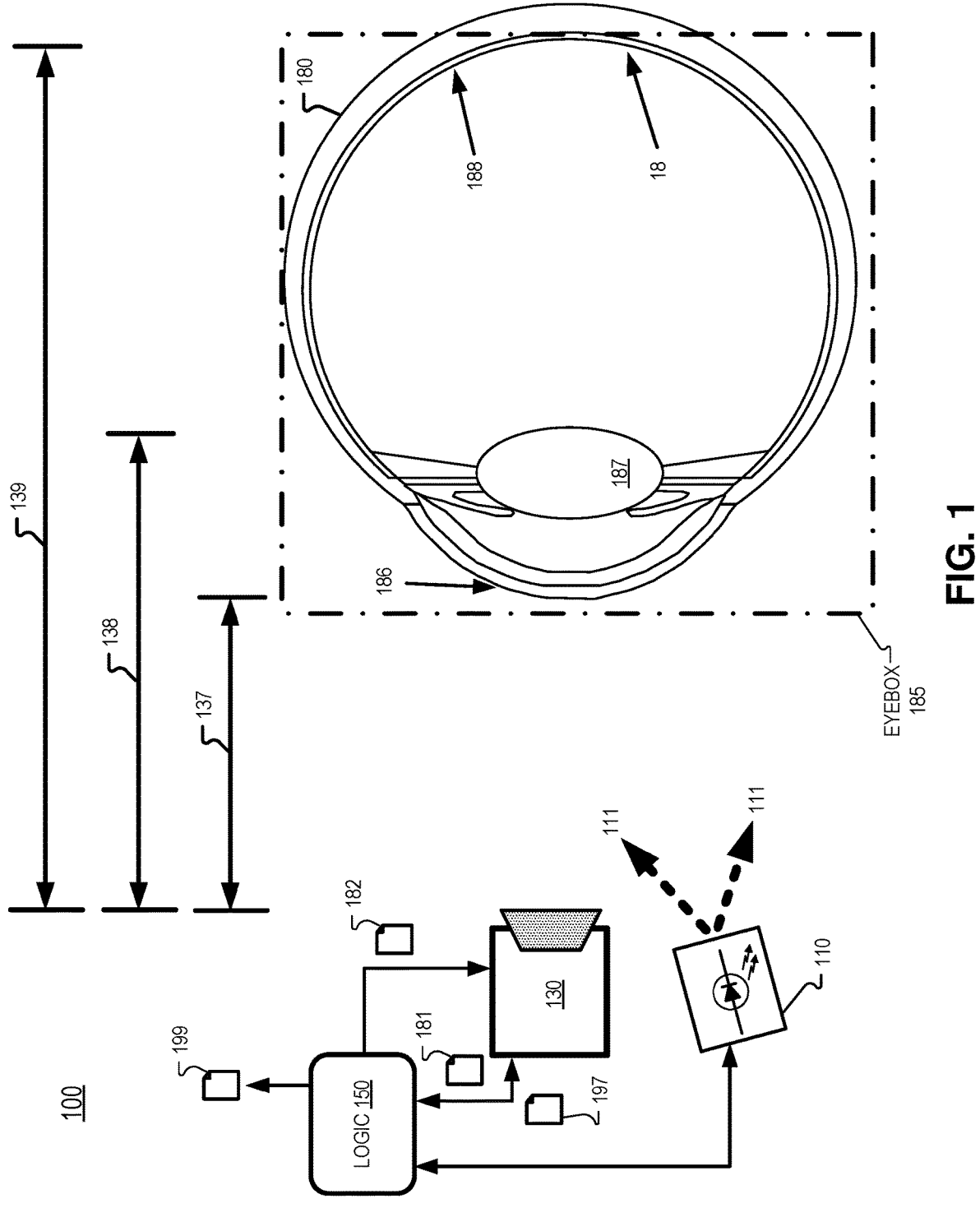
FIG. 1 illustrates a system including an imaging device, an illumination module, and processing logic, in accordance with aspects of the disclosure.

Embodiments of capturing images at varying optical powers are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In some implementations of the disclosure, the term "near-eye" may be defined as including an element that is configured to be placed within 50 mm of an eye of a user while a near-eye device is being utilized. Therefore, a "near-eye optical element" or a "near-eye system" would include one or more elements configured to be placed within 50 mm of the eye of the user.

In aspects of this disclosure, visible light may be defined as having a wavelength range of approximately 380 nm-700 nm. Non-visible light may be defined as light having wavelengths that are outside the visible light range, such as ultraviolet light and infrared light. Infrared light having a wavelength range of approximately 700 nm-1 mm includes near-infrared light. In aspects of this disclosure, near-infrared light may be defined as having a wavelength range of approximately 700 nm-1.4 μm.

In aspects of this disclosure, the term "transparent" may be defined as having greater than 90% transmission of light. In some aspects, the term "transparent" may be defined as a material having greater than 90% transmission of visible light.

In implementations of the disclosure, an imaging device includes an image pixel array and a plurality of micro-electro-mechanical systems (MEMS) Alvarez tunable lenses disposed over regions of the imaging pixels. In some implementations, the image pixel array includes single-photon avalanche diodes (SPADs). In an example implementation, MEMS Alvarez tunable lenses are disposed over regions that includes 25 imaging pixels (e.g. 5×5 matrix of imaging pixels). Processing logic may then drive the plurality of MEMS Alvarez tunable lenses to provide varying optical power to focus light to the imaging pixels during a plurality of image captures. The different images generated by the different image captures have different depths of field. The different images may be combined into a light field image.

The described system may be used to image an eyebox region for eye-tracking purposes. In some implementations, the eyebox is illuminated with non-visible light (e.g. near-infrared illumination light). Imaging the eyebox region at different depths of field may allow for faster imaging of the iris and the retina which are at different focus depths. These and other embodiments are described in more detail in connection with FIGS. 1-7.

FIG. 1 illustrates a system 100 including an imaging device, an illumination module, and processing logic, in accordance with implementations of the disclosure. System 100 captures images at varying focus depths by utilizing a MEMS Alvarez tunable lens. For purposes of this disclosure, a tunable Alvarez lens is a varifocal composite lens where lateral shifts of two optical components generate a change in optical power. The tunable Alvarez lens can be driven to different optical powers (corresponding to different focal lengths) by adjusting the lateral shift of the two optical components with respect to one another. The surfaces of the optical components may be described by cubic phase equations.

In the illustration of FIG. 1, imaging device 130 may include a camera having an image pixel array including a plurality of imaging pixels. A plurality of MEMS Alvarez tunable lenses may be disposed over regions of the imaging pixels in order to vary the focus depths of the imaging pixels in that region. By way of example and not limitation, processing logic 150 may drive one or more MEMS Alvarez tunable lenses in imaging device 130 with a focus signal 182. The focus signal 182 may drive one or more MEMS Alvarez tunable lenses to a particular focus depth 137, 138, or 139. While the MEMS Alvarez tunable lens is driven to a focus depth, processing logic 150 may also initiate an image capture signal 181 to capture an image 197 with the imaging pixel array while the MEMS Alvarez tunable lens is at the focus depth. Processing logic 150 may drive imaging device 130 to capture a plurality of images where imaging device 130 is focused to different focus depths in order to generate multiple images that can be combined into a light field image 199. Processing logic 150 may be configured to receive the one or more images 197 from imaging device 130. In some implementations, processing logic 150 is included in imaging device 130.

FIG. 1 shows that example system 100 may optionally include an illumination module 110 that generates illumination light 111. Processing logic 150 may drive illumination module 110 to selectively illuminate a subject with illumination light 111. In an implementation, illumination light 111 is non-visible light. In some implementations, illumination module 110 includes a near-infrared light source. The near-infrared light source may be an LED or a vertical-cavity surface-emitting laser (VCSEL), for example. Imaging device 130 may be configured to sense returning light that is the non-visible illumination light 111 reflecting or scattering from eyebox region 185. Processing logic 150 may be configured to drive the plurality of MEMS Alvarez tunable lenses in imaging device 130 to provide varying optical powers to focus the returning light to the imaging pixels during a plurality of image captures with the imaging pixels. Processing logic 150 may be configured to combine the image captures 197 at the varying optical powers into a light field image 199.

FIG. 1 illustrates that one example utilization of system 100 is to image an eyebox region 185 that includes an eye 180. Processing logic 150 may be configured to drive imaging device 130 to capture images at different focus depths. The illustrated example focus depths 137, 137, 139 correspond to object planes related to the cornea 186, lens 187, and retina 188, respectively. Hence, imaging device 130 may be able to achieve "whole-eye imaging" by imaging multiple planes of eye 180 rather than merely imaging the eye 180 on a single object plane. High-speed imaging of the eye 180 at multiple object planes is useful in eye-tracking contexts where depth information at different depths of the eye is useful.

Previous eye imaging techniques for eye-tracking were only for a single object plane. Or, previous imaging techniques that included multiple focal lengths (such as light field microscopy) were low resolution (and/or low speed) due to a single voxel being used to capture the image. Other prior imaging techniques used bulky lens actuators such as voice coils, bulk piezoelectric actuators, and shape-memory alloys. However, techniques that utilized these technologies were very slow (e.g. hundreds of milliseconds) and/or too bulky for most imaging applications.

Figure 2B:
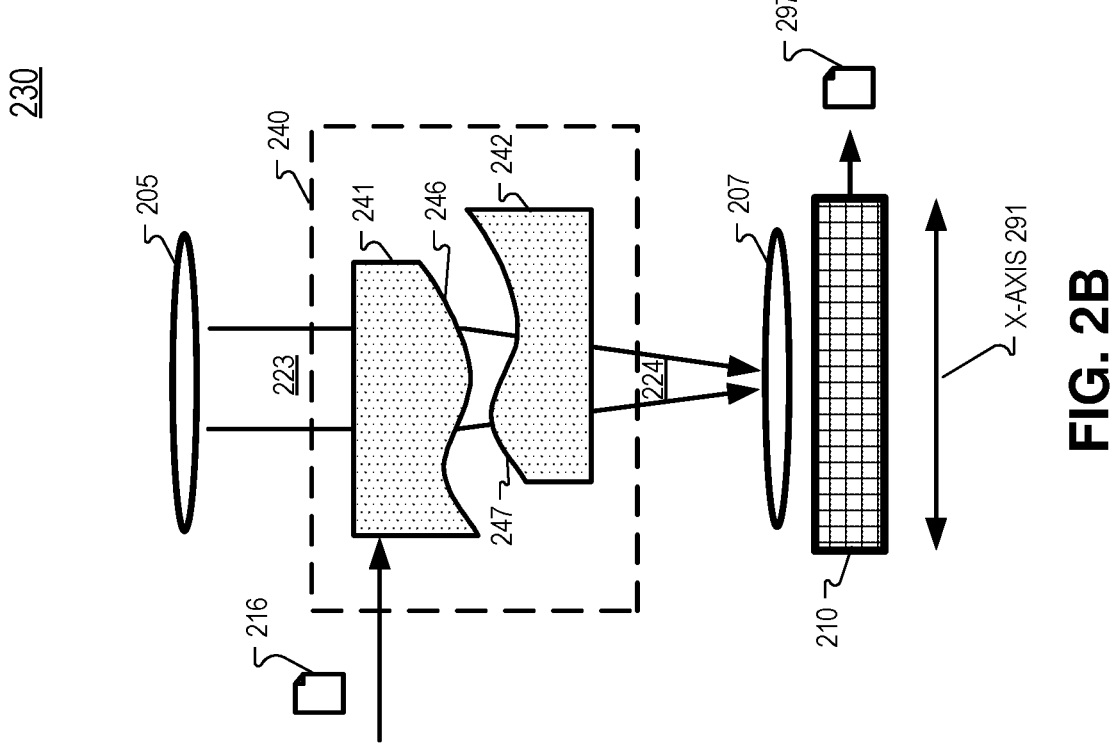
FIGS. 2A and 2B illustrate an example imaging device capturing images at different focus depths when an optical element of a MEMS Alvarez tunable lens is moved laterally along an axis, in accordance with aspects of the disclosure.
Figure 2A:
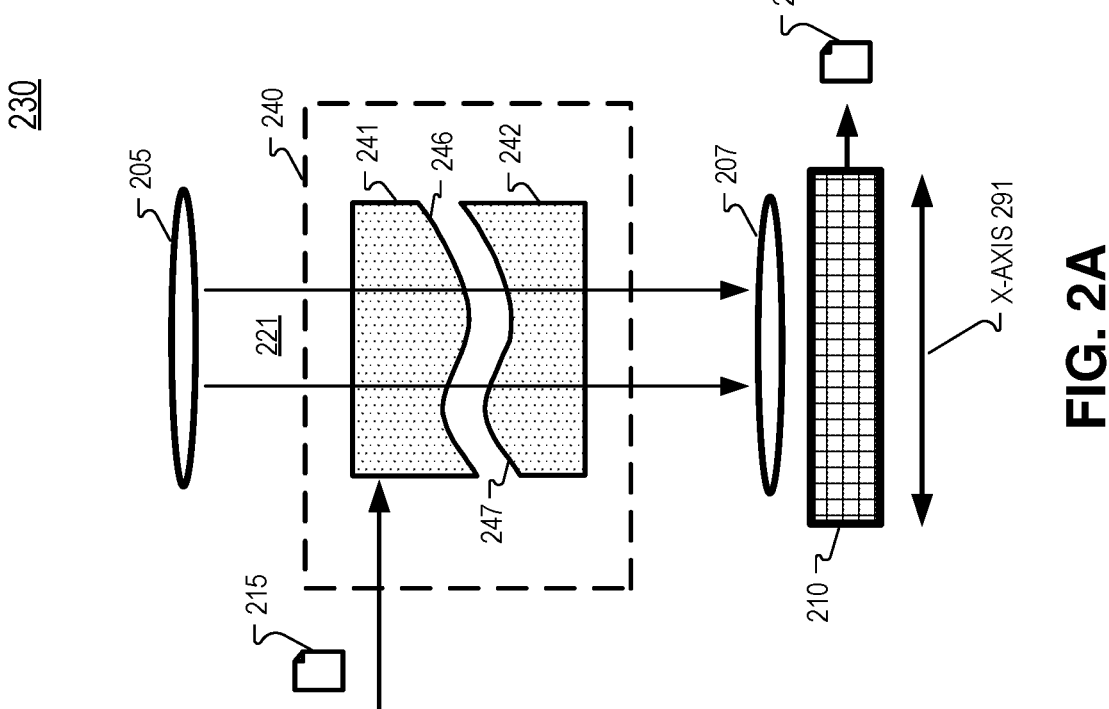

FIGS. 2A and 2B illustrate example imaging device 230 capturing images at different focus depths when an optical element of a MEMS Alvarez tunable lens is moved laterally along an axis, in accordance with aspects of the disclosure. The imaging device 230 of FIG. 2A includes an imaging pixel array 210 and a MEMS Alvarez tunable lens 240. In the illustrated implementation, optional lenses 205 and 207 are included in imaging device 230 to focus image light to an imaging plane of image pixel array 210. In the illustrated implementation, lens 207 is disposed between image pixel array 210 and MEMS Alvarez tunable lens 240 and MEMS Alvarez tunable lens 240 is disposed between lens 205 and lens 207. A filter (not illustrated) that passes a particular wavelength of near-infrared light (while rejecting other wavelengths) may be included in example imaging device 230. In an implementation, the filter passes a near-infrared wavelength that is matched to a near-infrared wavelength emitted by illumination module 110.

In some implementations, image pixel array 210 includes single-photon avalanche diodes (SPADs). Using SPADs as the imaging pixel in image pixel array 210 may increase the speed of the image captures.

The illustrated MEMS Alvarez tunable lens 240 includes a first optical element 241 and a second optical element 242. A first surface 246 of the first optical element may be defined by a cubic phase equation and the second surface 247 of the second optical element 242 may be defined by a different cubic phase equation.

First optical element 241 and a second optical element 242 provide varying optical powers when laterally shifted with respect to each other. In FIG. 2A, focus signal 215 drives MEMS Alvarez tunable lens 240 to traverse to a first position along x-axis 291 to provide a first focus depth to image pixel array 210. In the specific illustrated example of FIG. 2A, first optical element 241 is disposed above (and aligned with) optical element 242. Since first optical element 241 is aligned with second optical element 242 in FIG. 2A, MEMS Alvarez tunable lens 240 does not impart optical power to image light 221 because surfaces 246 and 247 have the same curvature. A first image capture 296 is initiated with image pixel array 210 while MEMS Alvarez tunable lens 240 is at the first position along x-axis 291.

In FIG. 2B, focus signal 216 drives MEMS Alvarez tunable lens 240 to traverse to a second position along x-axis 291 to provide a second focus depth to image pixel array 210. A second image capture 297 is initiated with image pixel array 210 while MEMS Alvarez tunable lens 240 is at the second position along x-axis 291. In the specific illustrated example of FIG. 2B, first optical element 241 is shifted along x-axis 291 while optical element 242 remains fixed. MEMS Alvarez tunable lens 240 imparts optical power to image light 223 to generate focused image light 224 for image pixel array 210 (when first optical element 241 is shifted along x-axis 291). A second image capture 297 is initiated with image pixel array 210 while MEMS Alvarez tunable lens is at the second position along x-axis 291 where the second image capture 297 is focused to the second focus depth.

While FIG. 2A and FIG. 2B illustrate just two different positions of MEMS Alvarez tunable lens 240, those skilled in the art appreciate that MEMS Alvarez tunable lens 240 may be driven to many different positions corresponding to different focal lengths (and focus depths) in order to capture multiple images at different focus depths.

Figure 3B:
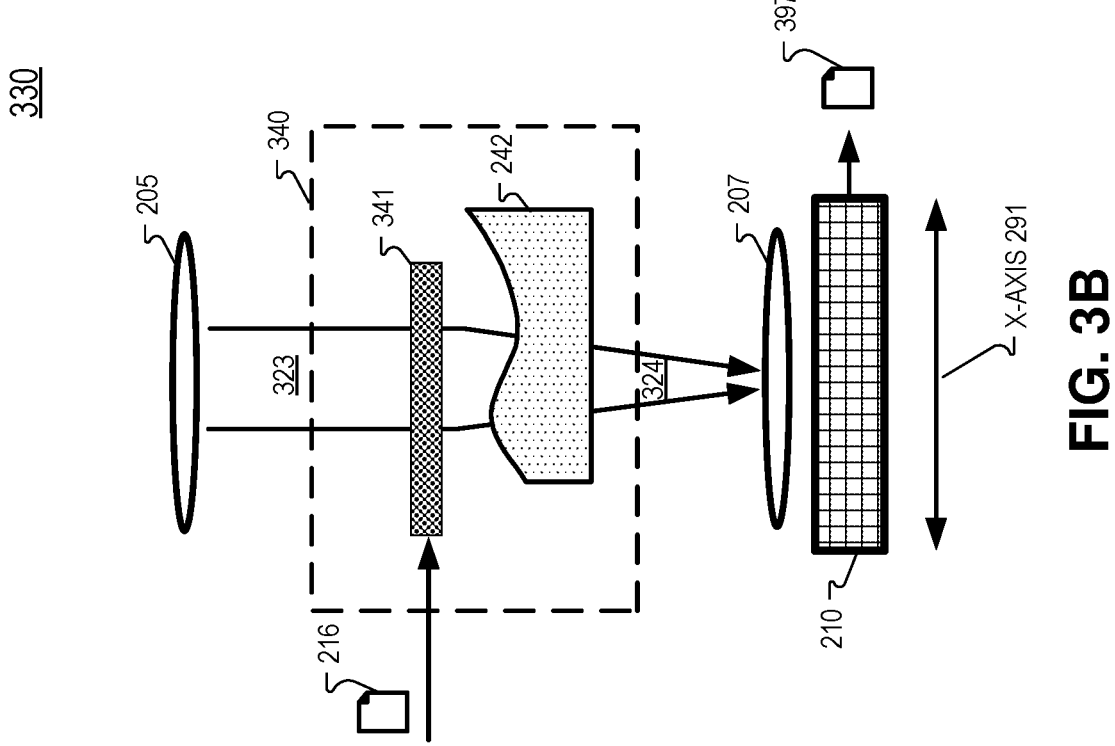
FIGS. 3A and 3B illustrate an example imaging device having a first optical element including a metasurface to provide varying optical power for a MEMS Alvarez tunable lens, in accordance with aspects of the disclosure.
Figure 3A:
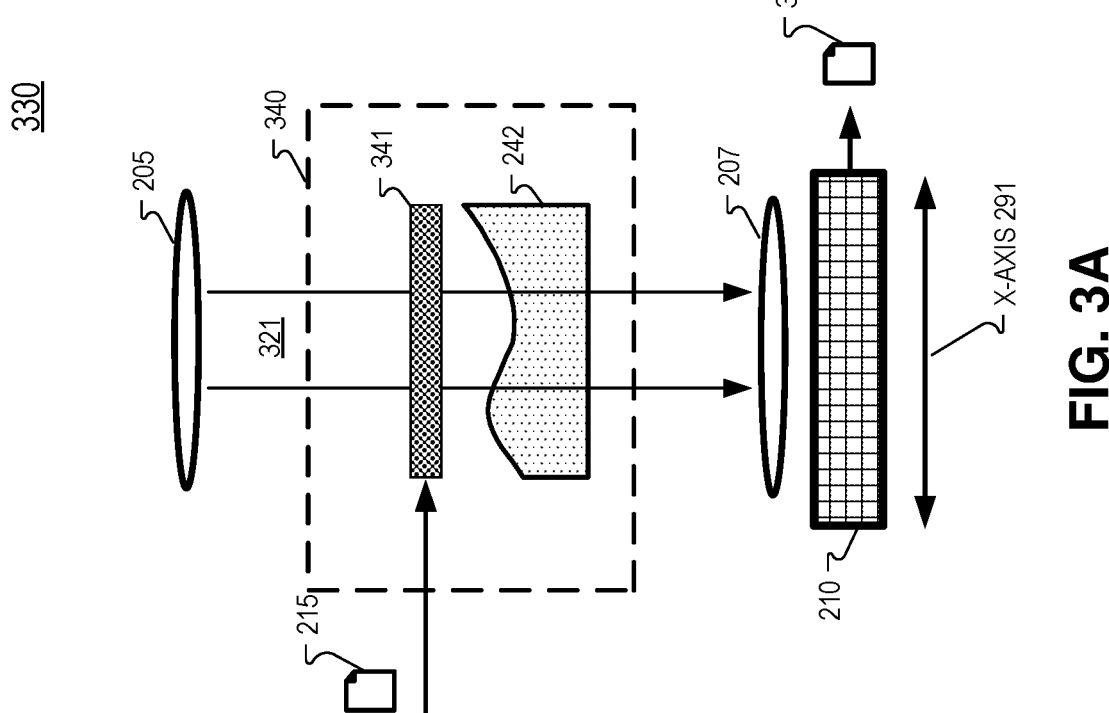

FIGS. 3A and 3B illustrate example imaging device 330 having a first optical element 341 including a metasurface to provide varying optical power for MEMS Alvarez tunable lens 340, in accordance with aspects of the disclosure. MEMS Alvarez tunable lens 340 is similar to MEMS Alvarez tunable lens 240 although first optical element 341 is a metasurface in FIGS. 3A and 3B. In contrast, the first optical element 241 in FIGS. 2A and 2B may be a refractive optical element.

In operation, first optical element 341 (metasurface) and second optical element 242 provide varying optical powers when laterally shifted with respect to each other along x-axis 291. First optical element 341 may be considered a metalens and may be advantageous because of its relative planar profile compared to a thicker refractive optical element. First optical element 341 may include discrete nano-structures such as pillars (varying in width and/or height) to create a designed diffractive lensing functionality. The lensing functionality imparted by the metasurface of first optical element 341 may be the same as the lensing functionality described by cubic phase equations in first optical element 241. In some implementations (not illustrated), both the first optical element and the second optical element of the MEMS Alvarez tunable lens include metasurfaces.

The metasurface of first optical element 341 may be tuned to diffract a narrow-band infrared wavelength (while passing visible light and wavelengths outside the narrow-band) according to a variable optical power as the first optical element 341 is moved along x-axis 291. The narrow-band infrared wavelength that the metasurface is tuned to may be matched to a narrow-band near-infrared wavelength emitted by illumination module 110.

First optical element 341 and a second optical element 242 provide varying optical powers when laterally shifted with respect to each other. In FIG. 3A, focus signal 215 drives MEMS Alvarez tunable lens 340 to traverse to a first position along x-axis 291 to provide a first focus depth to image pixel array 210. In the specific illustrated example of FIG. 3A, first optical element 341 is disposed above (and aligned with) optical element 242. While first optical element 341 is aligned with second optical element 242 in FIG. 3A, MEMS Alvarez tunable lens 340 does not impart optical power to image light 321. A first image capture 396 is initiated with image pixel array 210 while MEMS Alvarez tunable lens 340 is at the first position along x-axis 291.

In FIG. 3B, focus signal 216 drives MEMS Alvarez tunable lens 340 to traverse to a second position along x-axis 291 to provide a second focus depth to image pixel array 210. A second image capture 397 is initiated with image pixel array 210 while MEMS Alvarez tunable lens 340 is at the second position along x-axis 291. In the specific illustrated example of FIG. 3B, first optical element 341 is shifted along x-axis 291 while optical element 242 remains fixed. MEMS Alvarez tunable lens 340 imparts optical power to image light 323 to generate focused image light 324 for image pixel array 210 (when first optical element 341 is shifted along x-axis 291). A second image capture 397 is initiated with image pixel array 210 while MEMS Alvarez tunable lens 340 is at the second position along x-axis 291 where the second image capture 397 is focused to the second focus depth.

While FIG. 3A and FIG. 3B illustrate just two different positions of MEMS Alvarez tunable lens 340, those skilled in the art appreciate that MEMS Alvarez tunable lens 340 may be driven to many different positions corresponding to different focal lengths (and focus depths). Although FIGS. 2A-3B illustrate a first optical element being shifted laterally, the second optical element (closest to image pixel array 210) may also be shifted in a MEMS Alvarez tunable lens configuration.

Figure 4A:
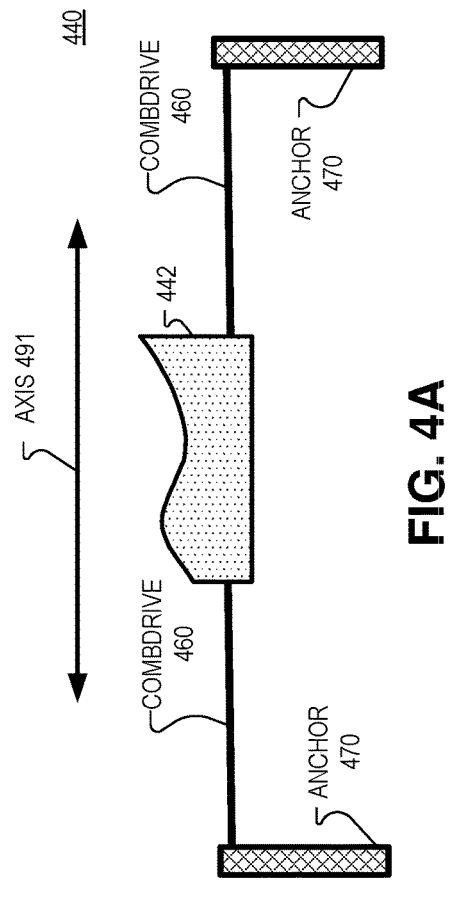
FIGS. 4A and 4B illustrate a sideview and a plan view of a combdrive mechanism to laterally shift an optical element along an axis, in accordance with aspects of the disclosure.
Figure 4B:
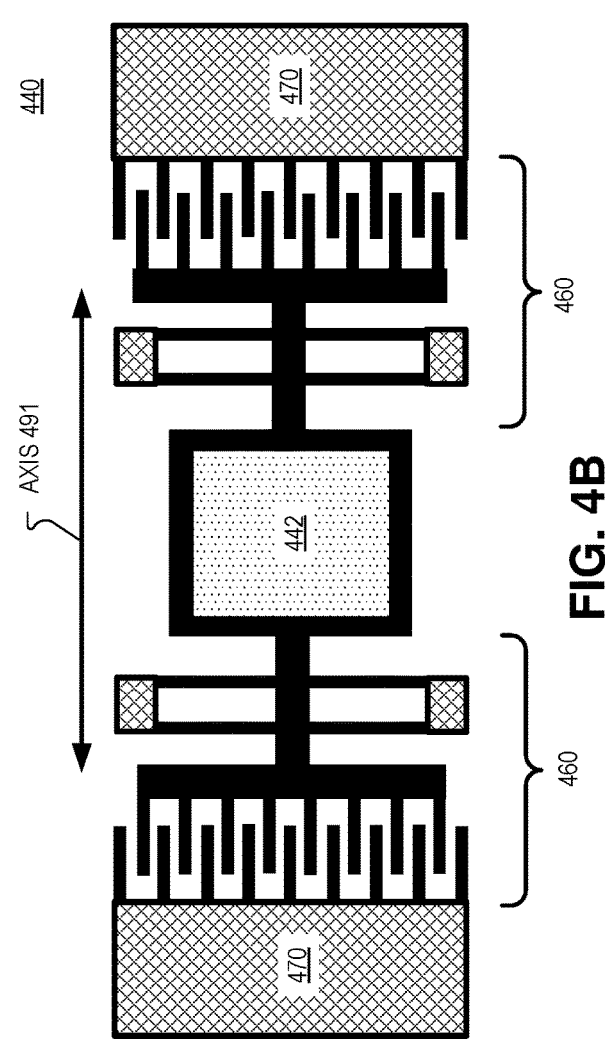

FIGS. 4A and 4B illustrate a combdrive implementation of a MEMS Alvarez tunable lens, in accordance with aspects of the disclosure. FIG. 4A illustrates a sideview of combdrive mechanism 440 to laterally shift an optical element 442 along an axis 491 and FIG. 4B illustrates a plan view of combdrive mechanism 440. Combdrive mechanism 440 includes anchors 470 coupled to combdrives 460. Optical element 442 is coupled between combdrives 460. To shift optical element 442 laterally along axis 491, a voltage is applied between static and moving combs of combdrives 460 to create an electrostatic force between them ultimately that shifts optical element 442 as optical element 442 is coupled to combdrives 460. While FIGS. 4A and 4B illustrate one example MEMS mechanism, other MEMS mechanism may also be used to shift an optical element of an Alvarez tunable lens.

FIG. 5A illustrates an example image pixel array 510 having an imaging plane defined in a two-dimensional x-y plane, in accordance with aspects of the disclosure. X-axis 591 and y-axis 592 define the imaging plane in FIG. 5A. Image pixel array 510 includes a plurality of imaging pixels. The image pixel array in FIG. 5A include x columns (C1, C2, C3, C4, C5 . . . . Cx) and y rows (R1, R2, R3, R4, R5 . . . . Ry) equating to n pixels (P1, P2, P3 . . . . Pn). Image pixel array 510 may be a SPAD image pixel array, in some implementations. The various disclosed MEMS Alvarez tunable lenses may be disposed over regions of the imaging pixels. FIG. 5B illustrates an example region 540 that a single MEMS Alvarez tunable lenses may be disposed over to focus image light to a plurality of the imaging pixels. Example region 540 include 25 pixels arranged in a 5×5 matrix, although different numbers of pixels and different geometric configurations may be included in regions in different implementations.

FIG. 5C illustrates that four MEMS Alvarez tunable lenses may be configured to focus image light to a plurality of imaging pixels (e.g. 25 imaging pixels per region) in corresponding regions 540. Hence, in FIG. 5C, four MEMS Alvarez tunable lenses focus image light for four regions 540, where each region 540 includes 25 imaging pixels. Thus, four MEMS Alvarez tunable lenses are used to focus the image light for 100 imaging pixels (P1, P2, P3 . . . . P99, P100), in FIG. 5C. The four MEMS Alvarez tunable lenses may be driven in concert by processing logic 150 to provide the same focus depth to the 100 pixels included in the four regions 540 during a first image capture. The four MEMS Alvarez tunable lenses may then be driven in concert by processing logic 150 to provide a different focus depth to the 100 pixels included in the four regions 540 during a second image capture. A plurality of MEMS Alvarez tunable lenses may continue being driven (in a synchronized manner) to different focus depths to progress through capturing images at different discrete focus depths in order to generate a light field image that includes the images of the subject at many discrete focus depths in a very short time period (e.g. less than 50 ms). The discrete focus depths may be evenly spaced or specifically programmed. For example, a light field image may include progressive focus depths that are 1 mm apart and processing logic 150 drives the MEMS Alvarez tunable lens to progressively capture images at the focus depths that are evenly spaced. In another example, a light field image may include specifically programmed focus depths such as a cornea focus depth, a lens focus depth, and a retina focus depth.

Figure 6:
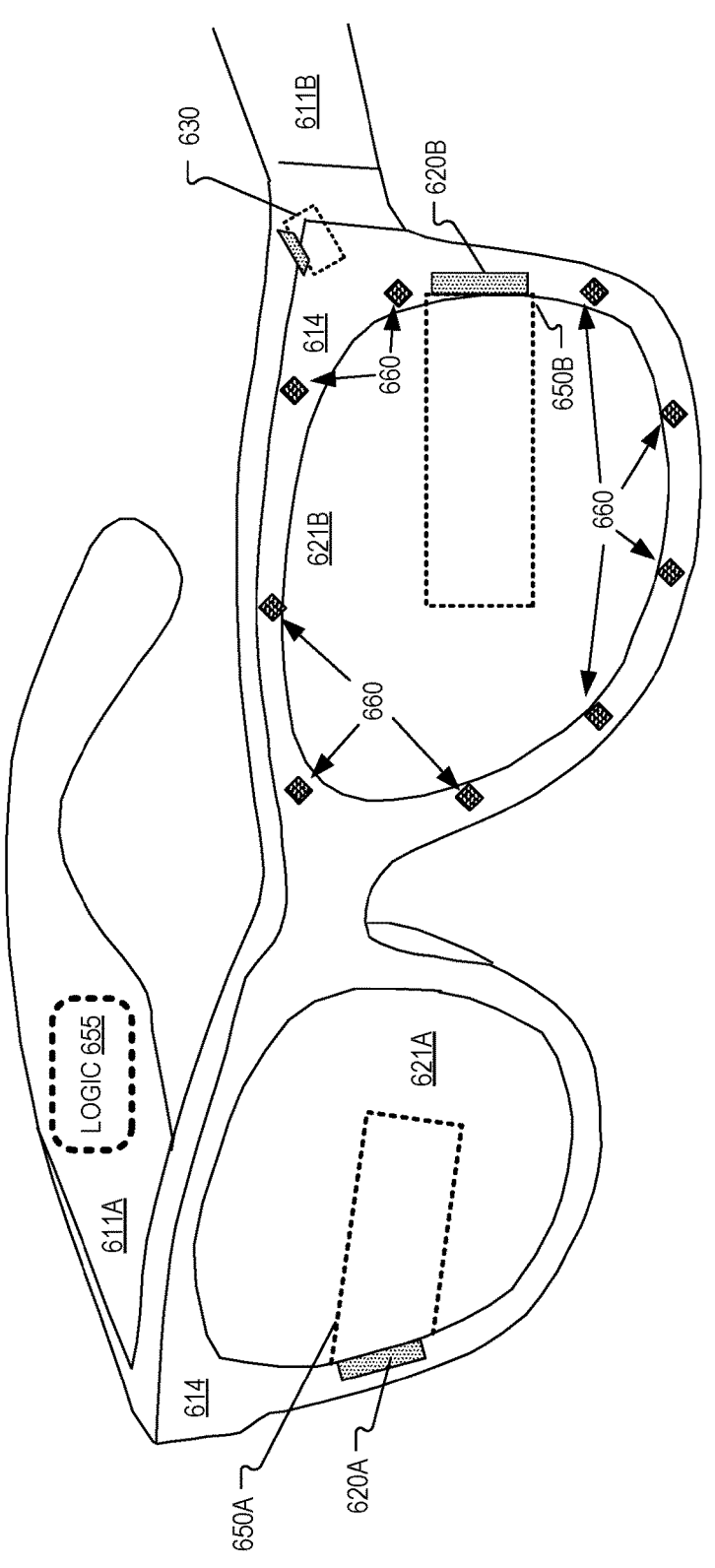
FIG. 6 illustrates an example head mounted device that may include an imaging device including MEMS Alvarez tunable lenses, in accordance with aspects of the disclosure.

FIG. 6 illustrates an example head mounted device 600 that may include an imaging device including MEMS Alvarez tunable lenses, in accordance with aspects of the disclosure. Head mounted device 600 includes frame 614 coupled to arms 611A and 611B. Lenses 621A and 621B (collectively referred to as lenses 621) are mounted to frame 614. Lenses 621 may be prescription lenses matched to a particular wearer of the head mounted device 600 or non-prescription lenses. The illustrated head mounted device 600 is configured to be worn on or about a head of a user.

In FIG. 6, each lens 621 includes a waveguide 650 to direct display light generated by a display 620 to an eyebox region for viewing by a wearer of head mounted device 600. Display 620 may include an LCD, an organic light emitting diode (OLED) display, micro-LED display, quantum dot display, pico-projector, or liquid crystal on silicon (LCOS) display for directing display light to a wearer of the head mounted device 600. The illustrated head mounted device 600 may be referred to as a head mounted display (HMD) since it includes at least one display 620 and waveguide 650 to present virtual images to a user. However, implementations of the disclosure may be utilized in head mounted devices (e.g. smartglasses) that don't necessarily include a display.

FIG. 6 illustrates example placements of illuminators 660 that are configured to illuminate an eyebox region with illumination light. The illumination light may be near-infrared light. The illuminators 660 may be LEDs or VCSELS, for example. Illuminators 660 may be included in illumination module 110, in some implementations.

Imaging device 630 is configured to image the eyebox region. Imaging device 630 is an example of how imaging device 130 may be positioned to image the eyebox region 185, in FIG. 1. Imaging device 630 may include the features of imaging device 130 including the MEMS Alvarez tunable lenses that may be driven by processing logic 655 to focus image light to an image pixel array.

Figure 7:
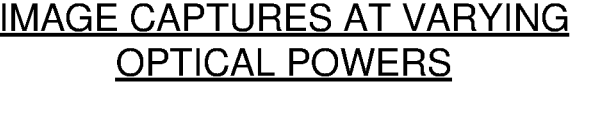
FIG. 7 illustrates a flow chart of an example process of capturing images at varying optical powers with a MEMS Alvarez tunable lens included in an imaging device, in accordance with aspects of the disclosure.
Figure 7:
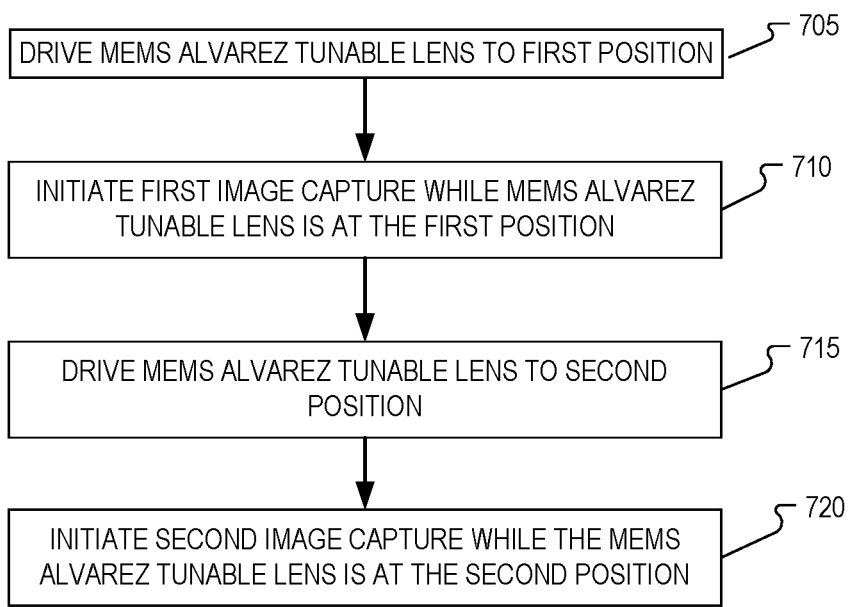

FIG. 7 illustrates a flow chart of an example process 700 of capturing image at varying optical powers with a MEMS Alvarez tunable lens included in an imaging device, in according with aspects of the disclosure. The order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel. All or a portion of the process blocks of process 700 may be executed by processing logic 150 or 655, for example.

In process block 705, a MEMS Alvarez tunable lens is driven to a first position along an axis to provide a first focus depth (e.g. focus depth 137). For example, a first optical element of the MEMS Alvarez tunable lens may be driven to a first lateral position with respect to a second optical element of the MEMS Alvarez tunable lens to focus image light to an image pixel array at a first optical power corresponding to the first focus depth. Processing logic 150 of FIG. 1 may drive a focus signal 182 that is received by imaging device 130 to drive a MEMS Alvarez tunable lens included in imaging device 130 to the first position.

In process block 710, a first image capture is initiated with an image pixel array (e.g. image pixel array 210) while the MEMS Alvarez tunable lens is at the first position. Processing logic 150 of FIG. 1 may send an image capture signal 181 to imaging device 130 to cause imaging device 130 to initiate a first image capture to generate a first image 197.

In process block 715, a MEMS Alvarez tunable lens is driven to a second position along the axis to provide a second focus depth (e.g. focus depth 138). For example, the first optical element of the MEMS Alvarez tunable lens may be driven to a second lateral position with respect to a second optical element of the MEMS Alvarez tunable lens to focus image light to the image pixel array at a different optical power corresponding to the second focus depth.

Processing logic 150 of FIG. 1 may drive a focus signal 182 that is received by imaging device 130 to drive the MEMS Alvarez tunable lens included in imaging device 130 to the second position.

In process block 720, a second image capture is initiated with the image pixel array while the MEMS Alvarez tunable lens is at the second position. Processing logic 150 of FIG. 1 may send an image capture signal 181 to imaging device 130 to cause imaging device 130 to initiate a second image capture to generate a second image 197.

In some implementations, the first image and the second image are combined into an aggregate image. In some implementations, many different images are captured at different focus depths in order to generate a light field image that images many different object planes in order to fully image the object at different focus depths. In the context of eye-tracking, having a light field image that includes focused images at varying depths allows for improved and more efficient eye-tracking since information from the cornea-plane, lens-plane, retina-plane, and other object planes can be imaged in the real time or pseudo real-time.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The term "processing logic" (e.g. processing logic 150 or processing logic 655) in this disclosure may include one or more processors, microprocessors, multi-core processors, Application-specific integrated circuits (ASIC), and/or Field Programmable Gate Arrays (FPGAs) to execute operations disclosed herein. In some embodiments, memories (not illustrated) are integrated into the processing logic to store instructions to execute operations and/or store data. Processing logic may also include analog or digital circuitry to perform the operations in accordance with embodiments of the disclosure.

A "memory" or "memories" described in this disclosure may include one or more volatile or non-volatile memory architectures. The "memory" or "memories" may be removable and non-removable media implemented in any method or technology for storage of information such as computer-readable instructions, data structures, program modules, or other data. Example memory technologies may include RAM, ROM, EEPROM, flash memory, CD-ROM, digital versatile disks (DVD), high-definition multimedia/data storage disks, or other optical storage, magnetic cassettes, magnetic tape, magnetic disk storage or other magnetic storage devices, or any other non-transmission medium that can be used to store information for access by a computing device.

Networks may include any network or network system such as, but not limited to, the following: a peer-to-peer network; a Local Area Network (LAN); a Wide Area Network (WAN); a public network, such as the Internet; a private network; a cellular network; a wireless network; a wired network; a wireless and wired combination network; and a satellite network.

Communication channels may include or be routed through one or more wired or wireless communication utilizing IEEE 802.11 protocols, short-range wireless protocols, SPI (Serial Peripheral Interface), I²C (Inter-Integrated Circuit), USB (Universal Serial Port), CAN (Controller Area Network), cellular data protocols (e.g. 3G, 4G, LTE, 5G), optical communication networks, Internet Service Providers (ISPs), a peer-to-peer network, a Local Area Network (LAN), a Wide Area Network (WAN), a public network (e.g. "the Internet"), a private network, a satellite network, or otherwise.

A computing device may include a desktop computer, a laptop computer, a tablet, a phablet, a smartphone, a feature phone, a server computer, or otherwise. A server computer may be located remotely in a data center or be stored locally.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A head mounted device comprising:
an illumination module configured to illuminate an eyebox region with non-visible illumination light;
an imaging device configured to sense returning light that is the non-visible illumination light reflecting or scattering from the eyebox region, wherein the imaging device includes:
an image pixel array including a plurality of imaging pixels; and
a plurality of micro-electro-mechanical systems (MEMS) Alvarez tunable lenses disposed over regions of the imaging pixels; and
processing logic configured to drive the plurality of MEMS Alvarez tunable lenses to provide varying optical powers to focus the returning light to the imaging pixels during a plurality of image captures with the imaging pixels, wherein the processing logic is configured to combine the image captures at the varying optical powers into a light field image.

2. The head mounted device of claim 1, wherein the image pixel array includes single-photon avalanche diodes (SPADs).

3. The head mounted device of claim 1, wherein the MEMS Alvarez tunable lenses include a first optical element and a second optical element that provide the varying optical powers when laterally shifted with respect to each other, and wherein the first optical element includes a first metasurface to provide the varying optical powers.

4. The head mounted device of claim 1, wherein the MEMS Alvarez tunable lenses include a first optical element and a second optical element that provide the varying optical powers when laterally shifted with respect to each other, and wherein the first optical element has a first surface defined by a first cubic phase surface, and wherein the second optical element has a second surface defined by a second cubic phase surface.

5. The head mounted device of claim 4, wherein the first cubic phase surface is the same as the second cubic phase surface.

6. The head mounted device of claim 1, wherein an imaging plane of the image pixel array is defined in a two-dimensional x-y plane, and wherein the MEMS Alvarez tunable lenses are adjusted along an x-axis of the two-dimensional x-y plane.

7. The head mounted device of claim 6, wherein the MEMS Alvarez tunable lenses include a combdrive to traverse along the x-axis.

8. The head mounted device of claim 1, wherein each of the MEMS Alvarez tunable lenses are configured to focus image light to a plurality of the imaging pixels in a corresponding region of the regions of the imaging pixels.

9. The head mounted device of claim 1, wherein providing the varying optical powers during the plurality of image captures includes:
driving the MEMS Alvarez tunable lenses to traverse to first positions along an axis to provide a first focus depth to the image pixel array;
initiating a first image capture with the image pixel array while the MEMS Alvarez tunable lenses are at the first positions;
driving the MEMS Alvarez tunable lenses to traverse to second positions along the axis to provide a second focus depth to the image pixel array; and
initiating a second image capture with the image pixel array while the MEMS Alvarez tunable lenses are at the second positions.

10. An imaging device comprising:

an image pixel array including a plurality of imaging pixels;

a plurality of micro-electro-mechanical systems (MEMS) Alvarez tunable lens disposed over regions of the imaging pixels, wherein the imaging device is configured to sense returning light that is a non-visible illumination light reflecting or scattering from an eyebox region; and processing logic configured to drive the plurality of MEMS Alvarez tunable lenses to provide varying optical powers to focus the returning light to the imaging pixels during a plurality of image captures with the imaging pixels, wherein the processing logic is configured to combine the image captures at the varying optical powers into a light field image.

11. The imaging device of claim 10, wherein the image pixel array includes single-photon avalanche diodes (SPADs).

12. The imaging device of claim 10, wherein the MEMS Alvarez tunable lens includes a first optical element and a second optical element that provide a first focus depth and a second focus depth when laterally shifted with respect to each other, and wherein the first optical element includes a first metasurface.

13. The imaging device of claim 10, wherein the MEMS Alvarez tunable lens includes a first optical element and a second optical element that provide varying optical powers when laterally shifted with respect to each other, and wherein the first optical element has a first surface defined by a first cubic phase surface, and wherein second optical element has a second surface defined by a second cubic phase surface.

14. The imaging device of claim 10, wherein a first focus depth is a cornea-plane and a second focus depth is a retina-plane.

15. The imaging device of claim 10, wherein an imaging plane of the image pixel array is defined in a two-dimensional x-y plane, and wherein the MEMS Alvarez tunable lens is adjusted along an x-axis of the two-dimensional x-y plane.

16. The imaging device of claim 15, wherein the MEMS Alvarez tunable lens includes a combdrive to traverse along the x-axis.

17. A system comprising:

an illumination module configured to illuminate an eyebox region with non-visible illumination light;

an imaging device configured to sense returning light that is the non-visible illumination light reflecting or scattering from an eyebox region, wherein the imaging device includes:

an image pixel array having a plurality of imaging pixels; and a plurality of micro-electro-mechanical systems (MEMS) Alvarez tunable lenses disposed over regions of the imaging pixels, wherein the MEMS Alvarez tunable lenses are configured to be adjusted to varying optical powers to focus image light to the plurality of imaging pixels at varying focus depths; and processing logic configured to drive the plurality of MEMS Alvarez tunable lenses to provide the varying optical powers to focus the image light to the imaging pixels during a plurality of image captures with the imaging pixels, wherein the processing logic is configured to combine the image captures at the varying optical powers into a light field image.

18. The system of claim 17, wherein the image pixel array includes single-photon avalanche diodes (SPADs).

19. The system of claim 17, wherein the MEMS Alvarez tunable lenses include a first optical element and a second optical element that provide the varying optical powers when laterally shifted with respect to each other, and wherein the first optical element includes a first metasurface to provide the varying optical powers.

20. The system of claim 17, wherein the MEMS Alvarez tunable lenses include a combdrive to traverse along an x-axis of an imaging plane of the image pixel array.

* * * * *